United States Patent
Passey et al.

(10) Patent No.: US 9,378,927 B2
(45) Date of Patent: Jun. 28, 2016

(54) AUTOSLICE AND VIEW UNDERCUT METHOD

(71) Applicant: FEI Company, Hillsboro, OR (US)

(72) Inventors: Richard Glen Ivy Passey, Corvallis, OR (US); John C. McNeil, Portland, OR (US)

(73) Assignee: FEI Company, Hillsboro, OR (US)

( * ) Notice: Subject to any disclaimer, the term of this patent is extended or adjusted under 35 U.S.C. 154(b) by 114 days.

(21) Appl. No.: 14/484,025

(22) Filed: Sep. 11, 2014

(65) Prior Publication Data

US 2016/0079035 A1    Mar. 17, 2016

(51) Int. Cl.
- *H01J 37/28* (2006.01)
- *H01J 37/317* (2006.01)
- *H01J 37/22* (2006.01)

(52) U.S. Cl.
CPC ........... *H01J 37/3177* (2013.01); *H01J 37/222* (2013.01); *H01J 2237/022* (2013.01); *H01J 2237/31749* (2013.01)

(58) Field of Classification Search
CPC combination set(s) only.
See application file for complete search history.

(56) References Cited

U.S. PATENT DOCUMENTS

| | | | |
|---|---|---|---|
| 7,858,936 B2 | 12/2010 | Bray et al. | |
| 7,977,631 B2 | 7/2011 | Mulders et al. | |
| 8,350,237 B2 | 1/2013 | Tanner | |
| 8,912,490 B2* | 12/2014 | Kelley | G01N 1/32 250/306 |
| 2006/0163497 A1 | 7/2006 | Kodama et al. | |
| 2006/0186336 A1* | 8/2006 | Giannuzzi | G01N 1/286 250/307 |
| 2007/0158566 A1 | 7/2007 | Ikeda | |
| 2009/0078867 A1 | 3/2009 | Avinun-Kalish et al. | |
| 2012/0217152 A1* | 8/2012 | Miller | H01J 37/3005 204/192.34 |
| 2013/0186747 A1* | 7/2013 | Schmidt | G01N 1/286 204/192.33 |
| 2013/0323937 A1 | 12/2013 | Kuebler | |

* cited by examiner

*Primary Examiner* — Phillip A Johnston
*Assistant Examiner* — Hsien Tsai
(74) *Attorney, Agent, or Firm* — James Wolfe; Michael O. Scheinberg; Scheinberg & Associates (57) ABSTRACT

A method is provided for slice and view processing of samples with dual beam systems. The slice and view processing includes providing a location for particles and material resulting from the slice and view process to collect without obscuring the sample face to be viewed and imaged. This location is formed as an undercut located beneath or in front of the sample face.

16 Claims, 6 Drawing Sheets

AUTOSLICE AND VIEW UNDERCUT METHOD

TECHNICAL FIELD OF THE INVENTION

The present invention generally relates to charged particle beam imaging for nanotechnology, and more particularly to a method for improving the acquisition of quality data during automated 3D analyses.

BACKGROUND OF THE INVENTION

Electron microscopy offers the opportunity to study material architectures in 3D at high resolution. This technique may be used to observe and analyze a variety of materials and used in different fields of applications. Although this invention is often utilized in the observation and analysis of semiconductors (e.g., via, transistors, etc.), it should be understood that the present invention is not limited to semiconductors and may include other materials such as metals, catalysts, polymers, and biological structures, for example. One technique employed with electron microscopy for analyzing materials, for example, is called "slice and view." This technique is typically performed with a system combining a focused ion beam (FIB) and a scanning electron microscope (SEM) such as the DualBeam® instruments commercially available from FEI Company, the assignee of the present invention.

Figure 1:
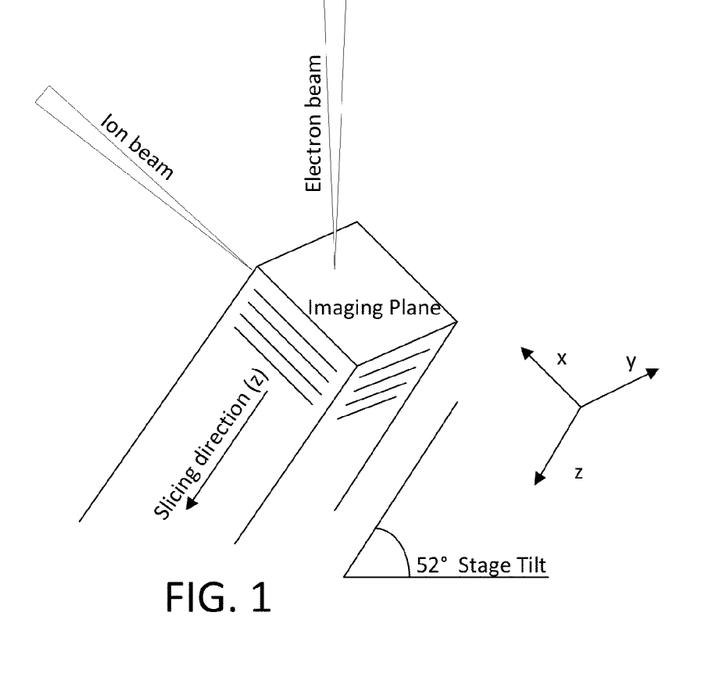
FIG. 1 is a diagram showing slice and view processing of a sample.

In the slice and view technique, as illustrated by FIG. 1, a feature of interest in a sample material is located and measured by known methods and techniques. The FIB cuts and slices the sample with high precision to reveal its 3D internal structures or features. Typically, the FIB exposes a cross section, or face, perpendicular to the top of the surface of the sample material having the hidden feature to be viewed. To further assist with separating a slice from the substrate material on each side of the area of interest is removed. Because the SEM beam axis is typically at an acute angle relative to the FIB beam axis, a portion of the sample in front of the face is preferably removed so that the SEM beam can have access to image the face. After obtaining an image of the face by the SEM, another layer of substrate at the face may be removed using the FIB, revealing a new, deeper face and thus a deeper cross-section of the feature. Since only the portion of the feature at the very surface of the face is visible to the SEM, sequential repetition of cutting and imaging, or slicing and viewing, is performed until the run is complete. This process provides the data needed to reconstruct the sliced sample into a 3D representation of the feature. The 3D structure is then used to analyze the feature.

Figure 2:
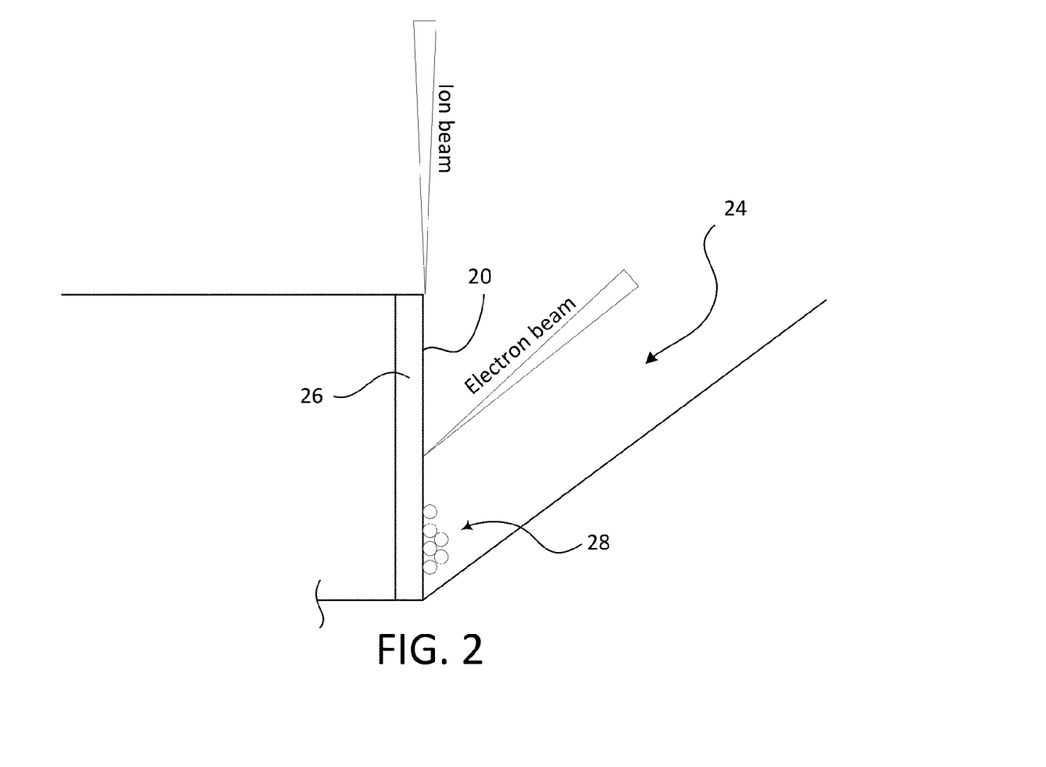
FIG. 2 is a side view diagram of a sample undergoing a standard slice and view processing showing material deposited onto the sample face.
Figure 3:
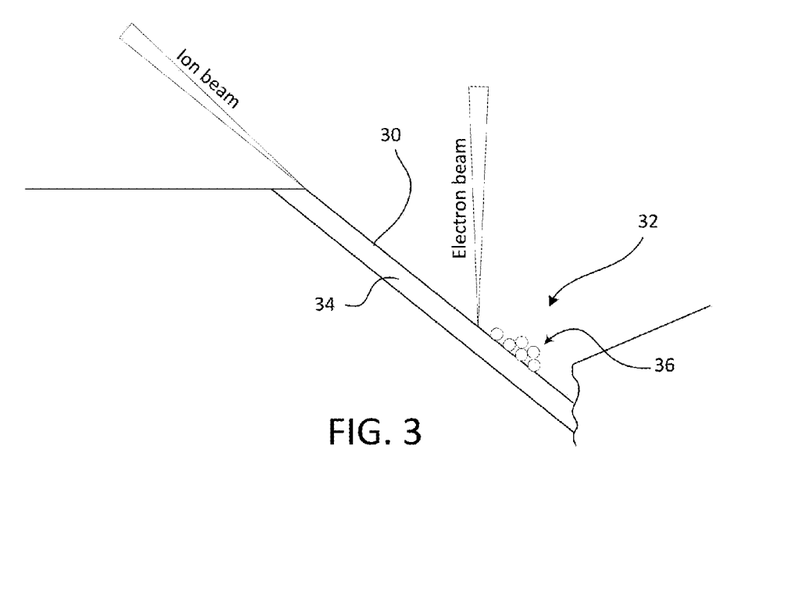
FIG. 3 is a side view diagram of a sample undergoing an angled slice and view processing with material deposited onto the sample face.

One problem that may occur while slicing away a layer of the substrate is redeposition. That is, particles of the remnant material may redeposit on the face of the feature to be imaged, preventing an unobstructed view of the face to be imaged causing an undesirable image resolution. This is best seen in FIG. 2, showing a standard slice and view method in which the FIB is normal to the top surface of the sample and the SEM is typically angled at about 52 degrees relative to the FIB axis. In this method, a vertical wall, or face 20, is exposed by removing material using the FIB to form a sloping trench 24. Once face 20 is exposed it is viewed for imaging by the SEM. A slice of material 26 may be removed using the FIB to expose a new face for imaging by the SEM. As the FIB performs the milling operation ablated material 28 from the area being milled and gallium from the ion beam may build up in front of and may be redeposited back onto face 20 altering or obscuring face 20. FIG. 3 illustrates the same problem in an angled slice and view method in which the SEM is normal to the top surface of the sample and the FIB is angled relative to both the SEM axis and the top surface of the sample. In this method, an angled face 30 is exposed by removing material using the FIB to form a trench 32. When face 30 is exposed it is viewed for imaging by the SEM. A slice of material 34 may be removed using the FIB to expose a new face for imaging by the SEM. As the FIB performs the milling operation ablated material 36 from the area being milled and gallium from the ion beam may build up in front of and may be redeposited back onto face 30 altering or obscuring face 20. The redeposited material in both FIGS. 2 and 3 leads to unusable data or failed automated cycles in which one poor quality slice or image can invalidate an entire run.

Figure 4:
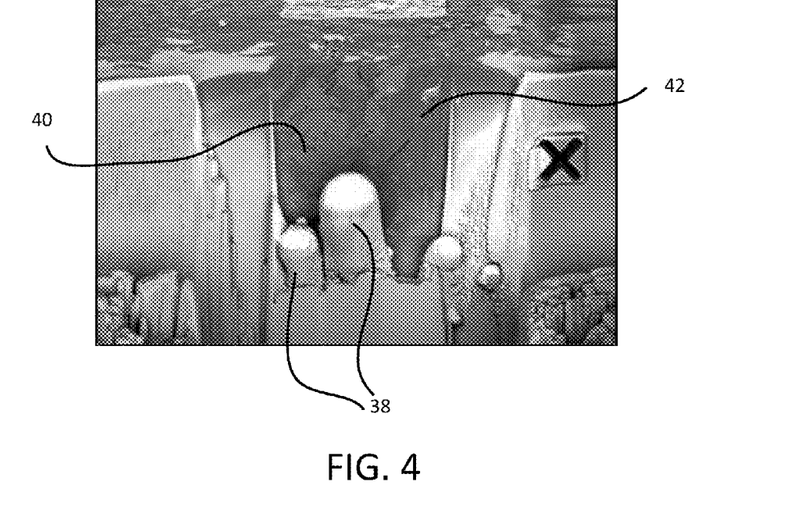
FIG. 4 is an image of a sample at the completion of slice and view processing with deposited material obscuring the sample face.

Software algorithms for 3D reconstruction from slice and view imaging generally assume that the surface of each slice imaged by the SEM is flat. The redepositioned material creates contrast and composition variations in which the material is interpreted as noise (e.g., decreased resolution) in the 3D representation formed from images of the exposed surfaces. For example, FIG. 4 shows a final image of a typical slice and view sample in which redeposition material 38 has built up to obscure and cast shadows 40 onto face 42 resulting in a flawed image. There is an increased demand for large volumes of flawless data because one poor quality slice or image can invalidate an entire run. Therefore, there is a need for a method that improves the acquisition of quality data from slicing process in a slice and view technique.

SUMMARY OF THE INVENTION

An object of the invention, therefore, is to provide a method for reducing or eliminating redeposition of ablated material in front of and/or onto a surface of a sample to be imaged in a slice and view process.

The present invention provides a method for milling multiple sequential cuts progressing into the face of a cross section wall. An undercut is made in the sample substrate beneath area of interest to be sliced and imaged. This undercut provides a physical space that separates the area of interest from the sample substrate to create a "trap" for the ablated material created by the milling process. This prevents the ablated material from being redeposited in a location that obscures the view of the milled face. This invention is applicable to both the standard and angled face methods of the slice and view process.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

According to preferred embodiments of the invention, a method provides slice and view techniques in which clear and unobstructed images of a sample are obtained to provide high quality data for 3D imaging. After determining the area of interest to slice and image, the area of interest is separated from the sample substrate by removing material in front of and on each side of the area of interest. An undercut is formed beneath the feature to be viewed to provide an area or trap to collect deposition material that results from the milling process.

Figure 5:
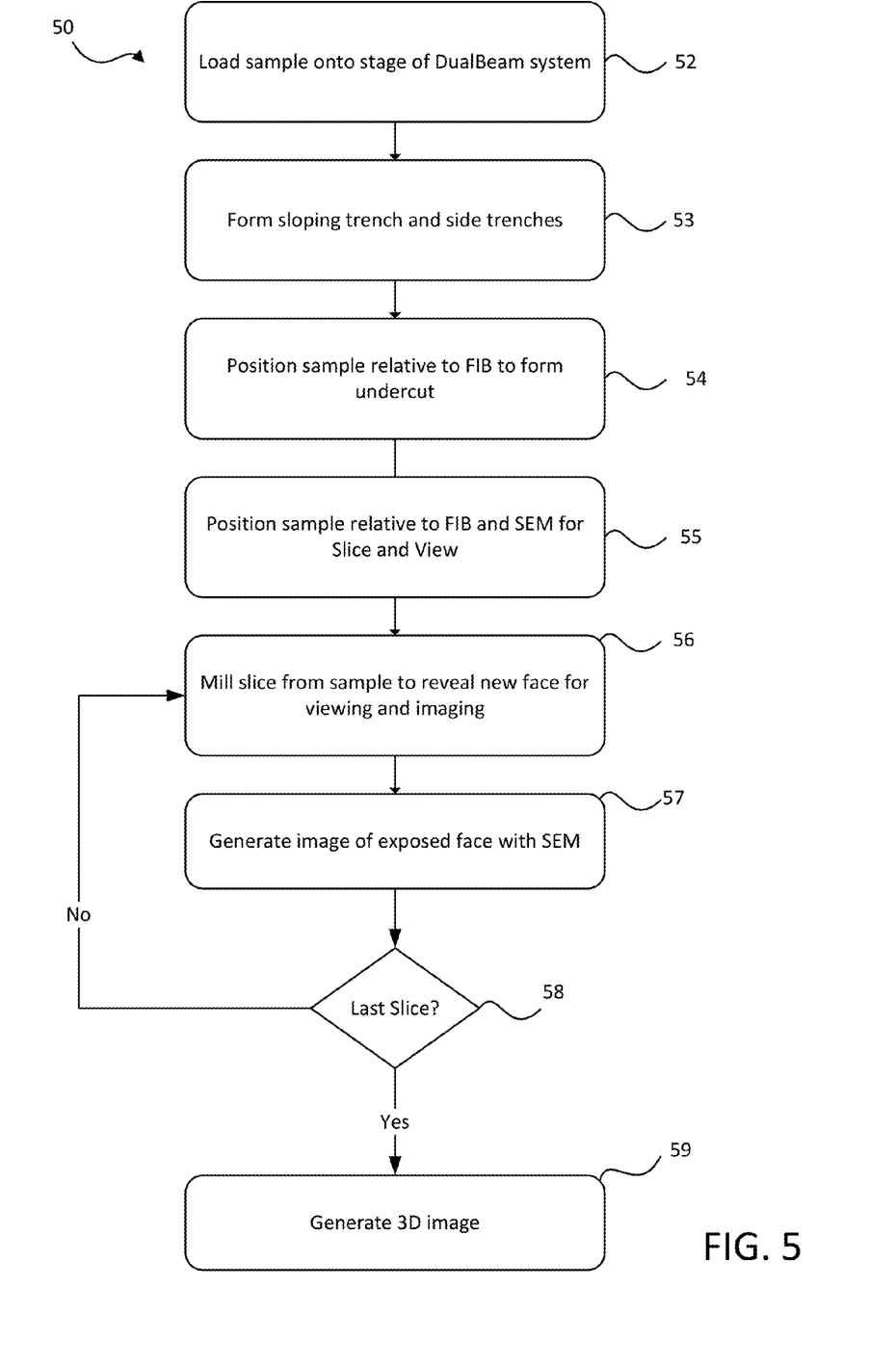
FIG. 5 is a flow diagram of a method of processing a sample by slice and view processing according to an embodiment of the disclosure.

Referring now to FIG. 5, a flow diagram of a method 50 for creating an image of a sample by slice and view processing with a dual beam system in accordance with an embodiment of the disclosure is shown. This technique may be performed with a system combining a focused ion beam (FIB) and a scanning electron microscope (SEM), such as the Dual-Beam® instruments commercially available from FEI Company, the assignee of the present invention. In order to remove material from the sample, the dual beam system of method 50 utilizes an etching beam, such as a focused ion beam from a FIB device or a laser beam from a laser. In order to image surfaces of the sample exposed by the etching beam, the dual beam system of method 50 utilizes an interrogating beam, such as an electron beam from a SEM. After the area of interest is determined, the sample is preferably mounted on a stage that is rotatable and/or translatable relative to the etching and interrogating beams, and rotation of the stage allows reorientation of the exposed surfaces so that the FIB can be utilized to remove material surrounding the feature to be imaged and to mill slices of the sample. Additionally, stage rotation allows images of the exposed surfaces to be taken from different perspectives, if desired. It should be noted that although the method 50 is explained using a focused ion beam from an FIB device, an electron beam from an SEM, a rotatable stage, and other specific elements, such selections are merely exemplary, and components capable of equivalent functions may be used.

The method 50 may begin at step 52 by loading a sample onto the stage of the dual beam system. In the standard slice and view method (FIG. 6) a sample 60 is mounted onto a stage of the dual beam system typically tilted to about 52 degrees from the horizontal so that the FIB impacts normal to a top surface 62 of sample 60 and the electron beam impacts the sample surface at about 52 degrees. In the angled face slice and view method (FIG. 7) the SEM is normal to top surface 70 of sample 72 and the FIB is angled relative to both the SEM axis and top surface 70. The angle of the FIB relative to the sample may be any desired angle. In one example, the FIB may be about 38 degrees relative to the top surface of the sample.

Figure 6:
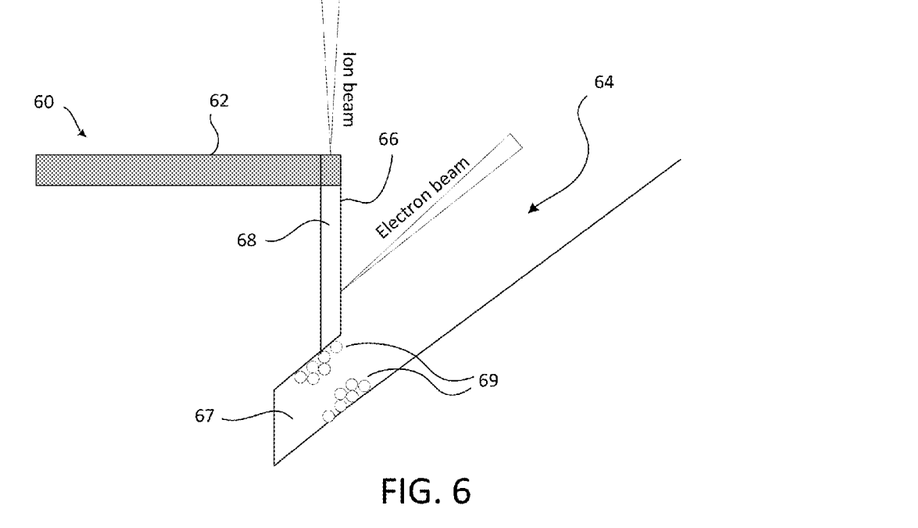
FIG. 6 is a side view diagram of a sample undergoing a standard slice and view processing with an undercut for deposited material.
Figure 9:
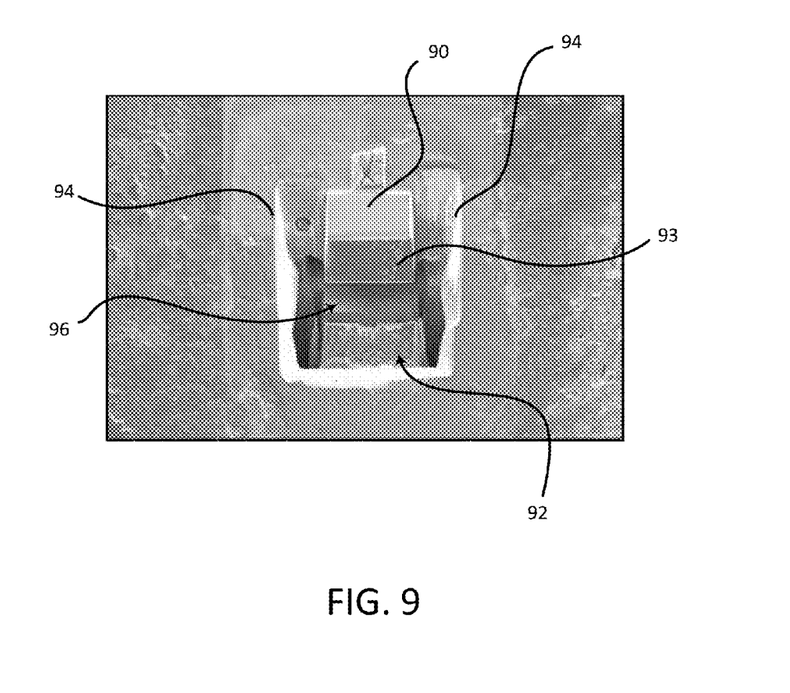
FIG. 9 is an image of a sample that has been prepared for slice and view processing with an undercut in accordance with an embodiment of the disclosure.

The method 50 may continue to step 53 where the focused ion beam is used to form a sloping trench to reveal a face for viewing and imaging and to form a side trenches on each side of the area of interest. As seen in FIG. 6, sloping trench 64 is formed in sample 60 using the focused ion beam to expose face 66 for viewing and imaging. Side trenches are also formed on each side of the area of interest as best seen in FIG. 9 where side trenches 94 are shown. The dimensions of the sloping trench and side trenches can vary depending on the dimensions of the area of interest. Dimensions are generally described as extending along x (width), y (length), and z (depth) axes as shown in FIG. 1. In one example, the area of interest may have an x-axis width of about 10 μm, a y-axis length of between about 12-15 μm, and a z-axis depth of about 10 μm. Sloping trench 64 may, for example, be milled approximately 35 μm back from face 66 containing the feature of interest. The x-axis width of sloping trench 64 including the side trenches is greater than that of the area of interest. Typically, each side trench has a width of about 30-35% of the width of the area of interest. For example, with a width of about 10 μm each side trench may be between about 3-4 μm so that the sloping trench has a total x-axis width of between about 16-18 μm. The angle of sloping trench 64 is sufficient so that both the focused ion beam and the electron beam can scan face 66 at the end of sloping trench 64. In this embodiment, face 66 is typically normal to surface 62 and runs parallel to the direction of the mill. In some embodiments, sloping trench 64 is dimensioned such that the electron beam may fully interrogate face 66 from two or more different orientations without obstruction by other surfaces of the sample.

The method 50 may continue to step 54 where the stage is reoriented relative to the FIB device to form an undercut 67 beneath face 66. The length of undercut 67 may vary depending on the dimension of the area of interest. For example, if the area of interest has a z-axis depth of about 6 μm the undercut preferably extends back at least about 6 μm. The y-axis length of undercut 67 may also vary but is preferably sufficient to provide a location for material resulting from the milling operation to collect without obscuring the face to be viewed and imaged. Undercut 67 may, for example, be formed having a y-axis length of about 5 μm from the lower edge of face 66 and may extend back along the z-axis depth away from face 66 a distance past the feature of interest or so that undercut 67 extends below the last slice to be milled.

The method 50 may continue to step 55 where the stage is then positioned so that the sample is again normal to the FIB device and about 52 degrees relative to the SEM. The method 50 may then continue to step 56 where, as shown in FIG. 6, a slice of material 68 is cut using the focused ion beam and then removed to reveal a new face. In some embodiments, the slice of material 68 is removed by milling an essentially one dimensional line running substantially parallel to the plane of face 66. The thickness of the slice to be removed may vary depending on the size of the feature contained within the area of interest. For example, in various embodiments, the thickness of the slice removed by the focused ion beam may be in a range of from about 20 nm to about 100 nm, such as in a range of from about 30 nm to about 60 nm. The width and length dimensions of the slice removed may be, for example, in a range of from about 10 μm to about 100 μm. As seen in FIG. 6, any particles of the remnant material or gallium from the ion beam resulting from milling a slice of the sample is deposited and collected within undercut 67 leaving face 66 unobstructed for viewing by the SEM.

The method 50 may continue to step 57 by capturing and storing an image of face 66 with an electron beam of a SEM in a manner known in the industry.

From step 57, the method may proceed to step 58 by determining whether to carry out another iteration of slice and view processing of sample (e.g., by repeating steps 56 and 57) or continue to step 59 by terminating slice and view processing of the sample and generating a 3-D image of feature of interest. To generate a 3-D image of the feature, it is desirable to obtain many images, depending on the size of the feature or the desired detail of the 3-D image. In block 58 the iterations of the slice and view technique are counted as processing of the sample progresses. In one embodiment, slice and view processing continues until a predetermined number of slice and view iterations have been carried out. Termination of slice and view iterations may alternatively be initiated in response to the occurrence of a particular trigger event or may depend on whether additional input is received by the slice and view processing system after a certain number of slice and view iterations have been carried out. In any case, if it is determined that slice and view processing of the sample should continue, the method 50 proceeds from step 56 to step 57 along the "No" path. If it is determined that the reiterative slicing process has concluded, the method 50 proceeds from step 58 to step 59 along the "Yes" path.

In step 59, a 3-D representation of the area of interest is generated from data gathered during slice and view processing of the sample using techniques that are well known. Providing a location for particles resulting from the processing to collect without obscuring the sample face allows high quality imaging to be obtained to produce an accurate and usable 3-D representation of the sample feature.

Figure 7:
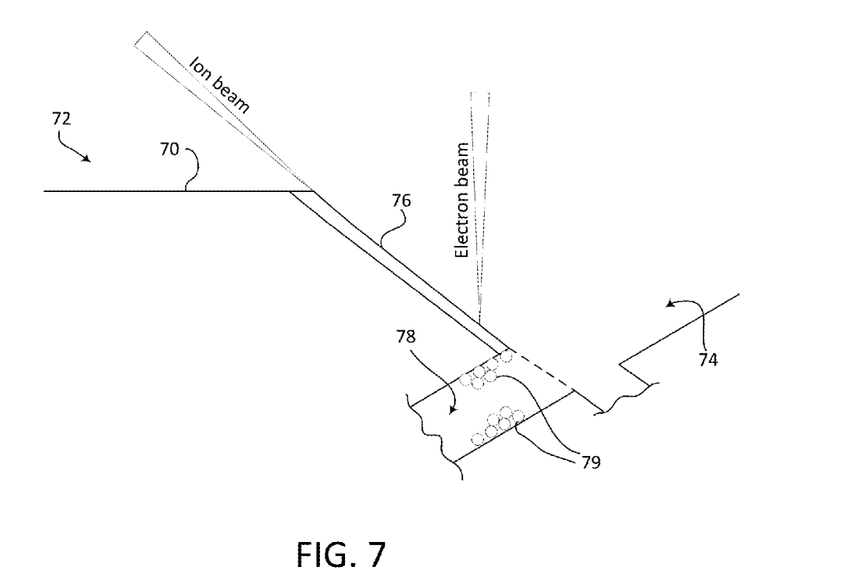
FIG. 7 is side view diagram of a sample undergoing an angled slice and view processing with an undercut for deposited material.

The method 50 is equally applicable to the angled slice and view method as seen in FIG. 7 in which the focused ion beam and electron beam are angled to any desired degree relative to surface 70 and sample 72. In this embodiment, sloping trench 74 is formed using the focused ion beam to reveal an angled face 76 that extends away from surface 70 at any desired angle. The stage is then reoriented relative to the FIB device to form an undercut 78 that extends beneath angled face 76. The focused ion beam then mills a slice in the same manner described above with reference to FIG. 6 except for the angled relationship of the focused ion beam and electron beam. As each slice is milled any particles 79 of the remnant material or gallium from the ion beam resulting from milling a slice of the sample is deposited and collected within undercut 78 leaving face 76 unobstructed for viewing by the electron beam.

Figure 8:
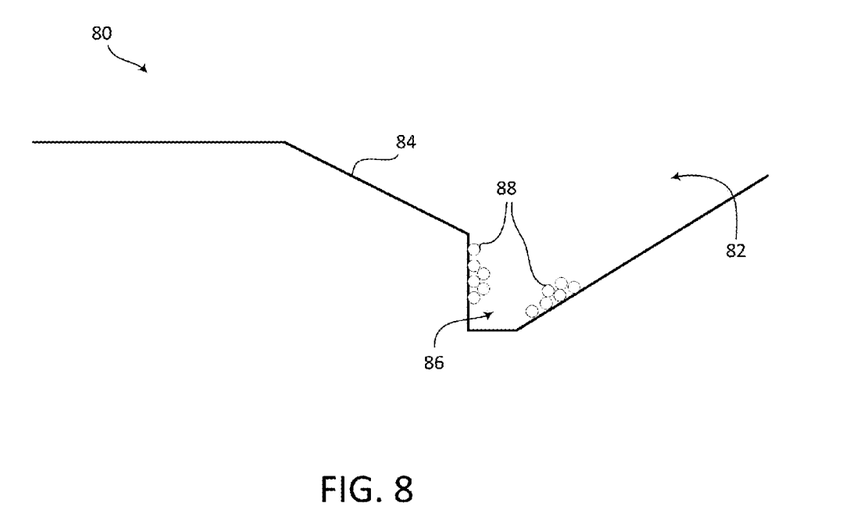
FIG. 8 is a side view diagram similar to FIG. 7 showing an alternative undercut for deposited material.

FIG. 8 shows an alternate shape for an undercut in the angled slice and view method similar to the angled slice and view method as shown and described in FIG. 7. In this embodiment, sample 80 is processed so that the focused ion beam (not shown) removes material to form sloping trench 82 to reveal an angled face 84 for viewing and imaging by the electron beam (not shown). An undercut 86 is formed in front of angled face 84 rather than extending underneath it as in the previous embodiment. Undercut 86 provides a location for particles 88 resulting from the slicing operation to collect without obscuring angled face 84.

Figure 10:
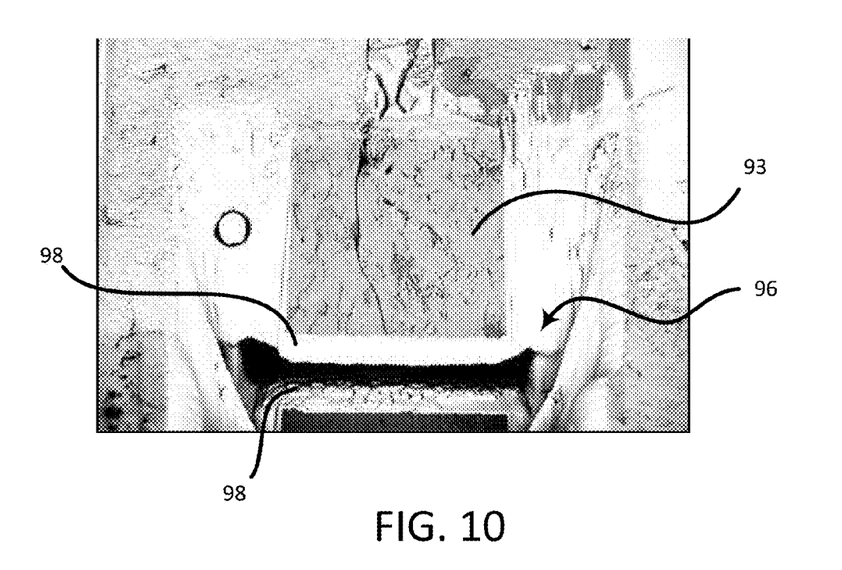
FIG. 10 is an image of a sample at the completion of slice and view processing with material deposited in an undercut.

FIG. 9 is an image of a sample that has been prepared for a slice and view process before the slice and view process is carried out. An area of interest 90 containing a feature of interest is located and isolated from the sample substrate by sloping trench 92 exposing face 93 to be viewed and imaged. Side trenches 94 separate area 90 from the sample substrate and undercut 96 is formed to collect and trap material resulting from the milling operation. FIG. 10 is an image of the sample of FIG. 9 at the completion of the slice and view process in which particles 98 accumulate in undercut 96 leaving face 93 free of any material deposition which would otherwise obscure viewing by the electron beam.

Some embodiments of the invention provide a method of processing a sample by slice and view processing with a dual beam system by locating an area of interest in the sample for viewing and imaging, exposing a face in the sample by removing material to create a trench, isolating the area of interest by removing material to form side trenches on each side of the area of interest, and creating a location for collecting particles resulting from the slice and view processing without obscuring the sample face. In some embodiments the location for collecting particles is formed as an undercut extending below the area of interest. In some embodiments the location for collecting particles is formed as an undercut located in front of the area of interest. Some embodiments include a face that is substantially perpendicular to a top surface of the sample while other embodiments include a face of the sample that is angled relative to the top surface of the sample. In some embodiments the area of interest has a depth and the location for collecting particles extends at least the depth of the area of interest.

Some embodiments of the invention provide a method of processing a sample by slice and view processing with a dual beam system by directing an ion beam toward a substrate to mill a trench in the substrate, the trench exposing a wall having an area of interest around a feature to be observed and directing the ion beam toward the substrate to mill a location for collecting particles resulting from the slice and view processing without obscuring the area of interest. In some embodiments the location for collecting particles is formed as an undercut extending below the area of interest and in other embodiments the location for collecting particles is formed as an undercut located in front of the area of interest. Some embodiments provide that the wall is substantially perpendicular to a top surface of the sample. Some embodiments provide that the wall is angled relative to the top surface of the sample.

Some embodiments of the invention provide a method of processing a sample by slice and view processing with a dual beam system by directing an ion beam toward a substrate to form a trench in the substrate so that the trench exposes a face in an area of interest of the sample to be observed; directing the ion beam toward the substrate to form an undercut extending lower than the trench; directing an electron beam toward the face to form an image of the face; and directing the ion beam to perform a milling operation by sequentially removing a plurality of slices from the area of interest revealing a new face with each new slice for viewing by the electron beam; wherein particles resulting from the milling operation are deposited and collected within the undercut without obscuring the face for viewing by the electron beam. Some embodiments provide that the face is substantially perpendicular to a top surface of the sample and that the undercut extends beneath the face of the sample. Some embodiments provide that the wall is angled relative to the top surface of the sample and that the undercut extends in front of the face.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of processing a sample by slice and view processing with a dual beam system, comprising:
    locating an area of interest in the sample for viewing and imaging;
    exposing a face in the sample by removing material to create a trench;
    isolating the area of interest by removing material to form side trenches on each side of the area of interest; and
    creating a location for collecting particles resulting from the slice and view processing without obscuring the sample face.

2. The method of claim 1, wherein the location for collecting particles is formed as an undercut extending below the area of interest.

3. The method of claim 1, wherein the location for collecting particles is formed as an undercut located in front of the area of interest.

4. The method of claim 1, wherein the face of the sample is substantially perpendicular to a top surface of the sample.

5. The method of claim 1, wherein the face of the sample is angled relative to the top surface of the sample.

6. The method of claim 1, wherein the area of interest has a depth, and the location for collecting particles extends at least the depth of the area of interest.

7. A method of processing a sample by slice and view processing with a dual beam system, comprising:
    directing an ion beam toward a substrate to mill a trench in the substrate, the trench exposing a wall having an area of interest around a feature to be observed; and
    directing the ion beam toward the substrate to mill a location for collecting particles resulting from the slice and view processing without obscuring the area of interest.

8. The method of claim 7, wherein the location for collecting particles is formed as an undercut extending below the area of interest.

9. The method of claim 7, wherein the location for collecting particles is formed as an undercut located in front of the area of interest.

10. The method of claim 7, wherein the wall is substantially perpendicular to a top surface of the sample.

11. The method of claim 7, wherein the wall is angled relative to the top surface of the sample.

12. A method of processing a sample by slice and view processing with a dual beam system, comprising:
    directing an ion beam toward a substrate to form a trench in the substrate, the trench exposing a face in an area of interest of the sample to be observed;
    directing the ion beam toward the substrate to form an undercut extending lower than the trench;
    directing an electron beam toward the face to form an image of the face;
    directing the ion beam to perform a milling operation by sequentially removing a plurality of slices from the area of interest revealing a new face with each new slice for viewing by the electron beam; wherein particles resulting from the milling operation are deposited and collected within the undercut without obscuring the face for viewing by the electron beam.

13. The method of claim 12, wherein the face is substantially perpendicular to a top surface of the sample.

14. The method of claim 13, wherein the undercut extends beneath the face of the sample.

15. The method of claim 12, wherein the wall is angled relative to the top surface of the sample.

16. The method of claim 15, wherein the undercut extends in front of the face.

* * * * *